United States Patent [19]

Saferstein et al.

[11] Patent Number: 5,919,471
[45] Date of Patent: Jul. 6, 1999

[54] SUBSTANTIALLY ANHYDROUS ANTISEPTIC WIPES

[76] Inventors: Lowell Saferstein, 14 Currey La., West Orange, N.J. 07052; Albert R. Kelly, 2 Cedar La., Douglaston, N.Y. 11363

[21] Appl. No.: 08/772,760

[22] Filed: Dec. 13, 1996

[51] Int. Cl.⁶ .................................................. A01N 25/34
[52] U.S. Cl. ........................................... 424/402; 424/404
[58] Field of Search ................................ 428/80; 252/91; 424/402, 484, 405, 435, 469, 448, 28

[56] References Cited

U.S. PATENT DOCUMENTS

| | | | |
|---|---|---|---|
| 4,310,509 | 1/1982 | Berglund et al. | 424/28 |
| 5,091,102 | 2/1992 | Sheridan | 252/91 |
| 5,322,695 | 6/1994 | Shah et al. | 424/448 |
| 5,492,692 | 2/1996 | Digenis et al. | 424/78.24 |
| 5,595,807 | 1/1997 | Gooding, Jr. et al. | 428/80 |
| 5,629,006 | 5/1997 | Hoang et al. | 424/405 |

*Primary Examiner*—Thurman K. Page
*Assistant Examiner*—William E. Benston, Jr.
*Attorney, Agent, or Firm*—Evelyn M. Sommer

[57] ABSTRACT

A substantially flexible, dry matrix with antimicrobial properties is made from a matrix comprising natural or synthetic, woven, non-woven or knitted fibers, said matrix having been uniformly coated with an amount of a non-aqueous treatment solution sufficient to allow said matrix to retain its substantially dry characteristics. In a preferred embodiment, said non-aqueous treatment solution has between about 70% and 99% of at least one glycol compound, between about 1% and 15% of a PVP-iodine and optionally between about 0 and 15% of a non-ionic surfactant.

Also, skin is treated to prevent disease, such as the disinfecting of teats on dairy cows during milking, by wiping the skin with the article.

21 Claims, No Drawings

SUBSTANTIALLY ANHYDROUS ANTISEPTIC WIPES

FIELD OF THE INVENTION

The present invention relates to an anhydrous wipe incorporating a non-aqueous solvent and an antimicrobial component, and optionally a nonionic surfactant. The dry wipe of the present invention can be used for a variety of sanitizing or disinfectant applications. For example, it can be used as an antiseptic hand and skin wipe, for first aid or wound care, for sanitizing and wiping the teats of dairy cows, and as a sanitizing dusting and cleaning cloth for hard surfaces.

The present invention also relates to a non-aqueous treatment solution containing an antimicrobial component, an optionally a nonionic surfactant.

BACKGROUND OF THE INVENTION

The external surfaces of various organisms such as humans, lower animals, and plants (e.g., "skin"), from time to time, need to be cleaned and, desirably, disinfected. For example, abrasions, skin infections, pre-surgical scrubs, various swellings, chronic inflammatory conditions, sprains, bruises, obstinate ulcers, and the umbilical stump of foals and calves need a disinfecting cleaning. Illustratively, to protect a dairy cow, its teats are cleaned before and after milking to reduce and/or prevent intramammary infections.

In this regard, in the late 1960's, the dairy industry adopted germicidal teat dipping to reduce the rate of new intramammary infections. Iodine based germicidal teat dips are recognized as effective and today, commercial teat dips frequently contain 0.5% or 1.0% active iodine aqueous solutions, and are sometimes formulated with an emollient such as 10% glycerine. An alternative aqueous teat dip currently in use contains povidone-iodine ("PVP-Iodine"). Such teat dips are either sprayed onto the teats or the teat is dipped into a cup of the disinfectant. In pre-milking, after the teat dip has been applied, a paper towel wipe is used to remove the excess dip 30–60 seconds after exposure. In post milking the germicidal solution is not wiped off.

However, various mastitis pathogens can be transmitted from infected to non-infected cows through the teat dipping cups and sprays often fail to contact the teat duct adequately and contribute to costly over spraying. Furthermore, the incorrect use of concentrated products such as udder washes or cleaners for teat dips can result in severe lesions within one or two applications. Improper mixing, freezing or simply production accidents also produce a variety of lesions. A further problem is that teat dips frequently dry out the teat skin, or, during extremely cold weather teat dips may promote teat chapping: teats exposed to extreme cold while wet with dip may freeze. Additional severe problems may occur when highly acidic utensil sanitizers or udder washes are used as teat dips. The use of such products, for even a few milkings, can cause severe teat lesions that may predispose to a serious outbreak of mastitis within a herd.

In 1996, Applied Microbiology launched Wipeout, a pre-moistened dairy wipe containing the antimicrobial peptide nisan. This wipe simultaneously applied a germicidal agent and cleaned the teats before the teat was attached to the milking machine. As these wipes incorporate an alcohol-in-water solution, their storage requires special barrier packaging and they have a limited shelf life. In addition, the add on weight of these pre-moistened towels increases the cost of shipping them.

Currently there are only two over-the-counter antimicrobial ingredients approved by both the U.S. Food and Drug Administration and the Environmental Protection Agency for use in skin antisepsis, first aid, wound care, and hard surface sanitizing or disinfecting applications.

The first, ethyl alcohol, has a long history of safe and effective use. However, there is a long list of negative attributes associated with the use of ethyl alcohol. It dries and irritates healthy skin and stings injured or abraded skin. Moreover, as ethyl alcohol is highly volatile, it dissipates rapidly and thus has a short duration of antimicrobial effectiveness. Other disadvantages of ethyl alcohol include its stringent regulation by governmental agencies, its ability to erode some metals, its ability to remove paint and varnish and its ability to delaminate some plastics.

The other approved antimicrobial ingredient, PVP-iodine, has a variety of uses in health care on both skin and hard surfaces. PVP-iodine also has negative attributes that limit its use. For example, aqueous iodophor solutions such as PVP-iodine temporarily discolor and irritate skin, and can also corrode some metals.

The problems associated with these antimicrobial ingredients and their relatively high cost have limited their usage. Less versatile, less expensive and less effective ingredients such as bleach are commonly used on hard surfaces, and either benzalkonium-chloride or Triclosan is typically used on skin, both as aqueous solutions.

The use of premoistened wipes to deliver aqueous solutions containing alcohol or Povidone iodine to sanitize skin or to disinfect hard surfaces is longstanding. But such wet wipes are expensive because they require barrier packaging to prevent evaporation or "dryout". Also contributing to the expense of such wipes is the need for special binder-free substrates for hydro-alcoholic formulations and starch-free substrates for aqueous iodophor formulations. Thus, the use of these ingredients has been limited and reserved for higher risk healthcare and medical environments where other considerations justify the higher costs.

Such prior art references as U.S. Pat. Nos. 3,227,614; 3,283,357; 4,257,924; and 4,692,374 and Australian Patent No. 72440/87 disclose systems of diluting active disinfectants and cleaning agents in a carrier, applying the surplus of the carrier containing the active ingredients onto a specific applicator material and subsequently drying the material with the carrier and active ingredient. These methods were used in the prior art because it was a convenient way to evenly disperse a specific amount of active ingredient on an applicator material. For example, U.S. Pat. No. 3,227,614 uses a mineral oil as a carrier and adds an excess of detergent to counteract and emulsify the oily properties of the mineral oil carrier. The other references noted above use water, alcohol or combinations thereof, all followed by a drying step.

U.S. Pat. No. 5,091,102, "Method of Making a Dry Antimicrobial Fabric" contacts a substantially dry antimicrobial treated skin wipe with water to activate the germicidal agent.

SUMMARY OF THE INVENTION

The desirability for developing a non-aqueous, water-free, anhydrous wiper delivery system for such anti-microbials is therefore driven by the apparent opportunity to significantly expand usage of these more effective anti-microbials, by significantly reducing the cost per use vs. aqueous systems, and simultaneously by minimizing or eliminating the problems of skin irritation or discoloration, and hard surface corrosion. Given the economic implausibility of developing an anhydrous alcoholic formulation for a wiper which could be used water-free, or the physical impossibility of developing an alcoholic system which could be water activated, our efforts focused exclusively on the potential for incorporating povidone-iodine at the approved concentrations of 5% to 10% into a waterless formulation which could be impregnated into a wiper that would be ready-to-use, as a leave on antiseptic skin lotion, a water rinseable antiseptic skin cleanser, or a hard surface sanitizing cleaning and dusting cloth.

A germicidal dairy wipe treated with a 1–15% solution of povidone iodine (0.1–1.5% active iodine) in propylene glycol has several advantages over iodophor teat dips. One wipe per cow is used thereby minimizing transfer of infection. The propylene glycol solvent is slow to evaporate thus maintaining the germicidal activity for a longer period of time. Propylene glycol is also an emollient which lubricates the teat surface and reduces skin irritation. The formulation does not stain the skin of the milker nor the cow's teat. The wipe is sufficiently soft and absorbent to effectively clean dirt off the teat while concomitantly disinfecting it. Teats treated with this formulation will not freeze in cold weather. Aqueous iodophor teat dips are prone to causing damage to teats in freezing weather. Additionally, while aqueous teat dips need to be stored in heated facilities, the wipes of the present invention will not freeze in the outdoors.

The transfer of PVP-iodine bactericidal agent from a treated wipe to skin through the intervention of a propylene glycol solution such as the dairy wipe is a specific example of the more general application of the transfer of any medicament soluble in propylene glycol. Anti-fungals, other topical anti-microbials, anti-inflamatories, anti-acne and hemorrhoidal medicaments could also be delivered from a wipe to skin without the need for water activation using propylene glycol solutions.

The present invention also provides a hard surface cleaning and sanitizing wipe which can be used to pick up and remove dust while sanitizing that surface. Thus, the present invention provides a dry wipe for cleaning and disinfecting skin and for cleaning and sanitizing hard surfaces.

The present invention further provides a non-aqueous treatment solution containing a non-aqueous solvent, a medicament effective in the environment of said non-aqueous solvent, and optionally, a nonionic surfactant.

The present invention relates to a matrix capable of being converted into a substantially flexible dry wipe. Alternatively, the matrix can be converted into an antimicrobial garment, an antimicrobial air filter, an antimicrobial mat, or a skin wipe. In each instance cited, the matrix or substrate, (referred to herein as the "matrix") is made up of natural or synthetic fibers, processed into a paper woven, non-woven or knitted forms, or any combinations thereof. The matrix is uniformly coated with a treatment solution in an amount sufficient to obtain the benefits of the invention and yet still feel dry to the touch as no water is added other than that naturally present in the matrix. Likewise, the treatment solution is substantially free of water. With the aforementioned criteria in mind, the treatment solution applied can range between about 20 and 75%, preferably between about 40% and 60%, of basis weight of the matrix, said solution preferably comprising between about 0% and 99% of at least one glycol compound, between 1% and 15% of an antimicrobial material, and optionally between about 0% and 15% of a nonionic surfactant. Further, the solution may also optionally contain effective amounts of one or more fragrances, preferably between about 0.1% and 5%.

DESCRIPTION OF THE PREFERRED EMBODIMENTS

Herein, the term "substantially dry matrix" refers to a matrix to which no water has been added other than the water naturally present in the matrix as manufactured. Typically, the matrix has a moisture content of less than about 5%, and preferably less than about 3%. The term also encompasses a finished product, i.e. a wipe, to which a non-aqueous treatment solution containing an antimicrobial component and optionally a nonionic surfactant have been applied. The matrix with the treatment solution normally feels dry, or lubricious, to the touch. The matrix containing the substantially treatment solution used in the present invention may contain natural or synthetic fibers which may be processed into a woven, a nonwoven or a knitted form, a flexible foam, or combinations thereof. Of particular interest for use in the matrix employed in the present invention are the following fibers: polypropylene, polyester, nylon and cellulosics, such as cellulose, cotton, rayon, and hemp.

Typically, the matrix has a basis weight range generally of 5 to 200 grams per square yard, preferably 15 to 100 grams per square yard.

The skin wipe and other antimicrobial or germicidal embodiments of the present invention contain a topical antiseptic that is soluble in propylene glycol or a similar non-volatile nonaqueous solvent such as glycerine, or low molecular weight polyethylene glycol which can be impregnated into a substrate at a sufficiently high add on level so that the formulation is effectively transferred to skin upon wiping. Preferably, the medicament does no require water for activation.

PVP-Iodine is a stable chemical complex of polyvinylpyrolidone (PVP) and elemental iodine and this complex is the preferred medicament of the present invention. Commercially, the complex is available in a pharmaceutical grade containing 10 parts active halogen per 100 parts of dry powder. For this reason, the commercial product has sometimes been referred to as "PVP-Iodine 10".

There are two major suppliers of PVP-Iodine: BASF Fine Chemicals and Napp Technologies. PVP-iodine is completely soluble in cold water with mild agitation as well as propylene glycol in amounts up to and exceeding 10% (1.0% available iodine).

In general, to reduce germs on skin and prevent infections in skin, topical solutions containing between about 1 and 15% PVP-Iodine (0.1 and 1.5% available iodine) may be used. It is preferred that the solution contain between about 5 and 10% PVP-Iodine (0.5 and 1% available iodine), and most preferably the solution contains about 10% PVP-iodine (1% available iodine). The PVP-Iodine film should remain on the skin so that it can act as a continued microbial barrier.

One way to measure the efficacy of the treatment solution of the present invention as a surgical scrub is to take samples of the scrub juices to establish the immediate, cumulative and persistent effects. The immediate effect is the reduction in the bacteria count immediately after scrubbing. A cumulated effect is seen when regular use of the treatment solution leads to increasing reduction in the bacteria count. The persistence of the effect, is a decline in the post-wash bacterial count. Studies with PVP-iodine scrubs showed an effective, extensive immediate effect, a definite cumulative effect, as well as a persistence of the effect.

Chlorhexidine digluconate at 0.5% concentration in water is another antimicrobial solution currently used, typically as a teat dip. While chlorhexidine digluconate is not soluble in propylene glycol, chlorhexidine diacetate is soluble in propylene glycol. The diacetate is commercially available as a dry powder and 0.5% solutions of chlorhexidine diacetate are readily prepared.

The specific amounts of any particular antimicrobial which may be employed within this range will depend on such factors relating to the intended use of the article as can be readily determined by one of ordinary skill in the art.

The nature of the substrate dictates that amount of add-on needed to achieve effective transfer of the germicidal agent from wipe to skin. Synthetic fibers such a polyester or polypropylene transfer readily and thus less add on is required, however, substrates made from 100% of these synthetic fibers are harsh, non-absorbent and make poor wipes. On the other hand, 100% rayon fabrics are soft, highly absorbent and will retain the treatment formulation strongly and therefore do not transfer the treatment readily from substrate to skin. Blends such as 70% rayon, 30% polyester or 50:50 blends offer a good balance between softness and transfer of treatment upon wiping of skin. More preferred blends have between about 50 and 70% rayon and between about 30 and 50% polyester.

Using a 70:30 rayon, polyester blend for the substrate treatment levels of 50–60% add on were found to be optimal for effective transfer of treatment of solution from the wipe to the skin. Unlike the aqueous povidone-iodine teat dips, a wipe containing a propylene glycol solution of povidone-iodine does not stain or discolor skin. Moreover, the glistening of the propylene glycol on the skin imparts a shine which marks the area of treatment.

Depending upon the specific end use to which the article of the present invention is to be put, the treatment solution may also optionally contain from about 0.5% to 15% of a non-ionic surfactant in addition to the non-aqueous solvents specified herein. It is preferred that the treatment solution contains between about 3 and 6% of a non-ionic surfactant. The specific amount of the particular nonionic surfactant which is employed within this range will depend upon the detergent activity desired as can be readily determined by one of ordinary skill in the art; i.e., in applications requiring heavy duty cleaning power, higher amounts of nonionic surfactants in the treating solution would be used; and vice versa. Any of the well known classes of non-ionic surfactants such as nonylphenolethoxylates as Igepal may be employed in the wipe of the present invention.

When the treated substrate functions as a germicidal wipe, the non-ionic surfactant enhances the wipes cleaning function. If the povidone-iodine treated substrate functions as a germicidal wound covering, then the non-ionic surfactant can be left out.

The dry article, optionally, may contain one or more fragrances for imparting a pleasant odor to the cleaned surface as used herein, the term "fragrance" includes chemicals which can mask unpleasant odors and/or destroy unpleasant odors. When employed, the fragrance is present in the dry wipe in amounts up to 5% of the treatment solution.

Unlike aqueous PVP-iodine treatment solutions, in which water is only the carrier for the PVP-iodine, the present invention uses a non-aqueous solvent carrier. Glycols are the preferred non-aqueous solvents and propylene glycol is the preferred glycol. The non-aqueous solvent functions not only to dissolve the PVP-iodine, but these solvents also impart emolliency and lubricity to the treatment solution which helps prevent skin breakdown and maintain skin softness.

The use of propylene glycol instead of water as a solvent has several advantages. Propylene glycol is less volatile than water and thus evaporates more slowly. Propylene glycol is a lubricious emollient imparting soothing and softening qualities to skin. Propylene glycol does not freeze in cold weather.

Unlike the water in aqueous solutions of PVP-iodine such as Betadine™, propylene glycol is an active skin lubricant and emollient as well as the solvent for the PVP-iodine. The propylene glycol is a preferred component of the formulation and remains in contact with the skin for a long time after use. Typically, propylene glycol is the major component in the treatment solutions of the present invention. However, it can be replaced, in whole or in part, with similar glycols such as glycerine or low molecular weight polyethylene glycols such as PEG-200, PEG-400 etc. Preferably, not more that about 40% by weight of the propylene glycol is replaced with these other glycols.

The matrix prepared in accordance with one the methods described above, from which the cleansing wiper or other products of the present invention are obtained, can be coated and impregnated using any conventional process. Illustratively, continuous rolls of the matrix are passed between an engraved roll and a smooth rubber roll under pressured nip contact. The engraved roll is constructed of steel or other suitable material whose surface has been engraved with a plurality of cells or cavities that are defined by specific shape and dimensions. Said shape and dimensions determine the volume of liquid picked up and held in the said cavities when in use.

During operation, the engraved roll is partially submerged in the treatment solution described previously and rotates therethrough, causing said solution to fill the cavities of the engraved portion of said engraved roll. Excess solution accumulating above the plane of the engraving is removed by a doctor blade. The solution remaining in the cells of the engraved roll is caused to transfer by way of pressure absorption and surface tension into the matrix as it passes under pressure between said engraved roll and rubber roll.

Thereafter, the treated matrix containing the measured volume of treatment solution may be wound onto rolls and/or converted into the desired product. For the purposes of this specification, the term "conversion" means the process(es) of modifying the physical characteristics of the treated matrix by such conventional methods as ereping embossing, laminating, slitting, and cutting so that the treated matrix is rendered into a form that is saleable as a manufactured product and is ready for distribution.

An important requirement of this method for treating said matrix with the treatment solution is that the linear speed of the matrix passing through the nip formed by the engraved roll and rubber must equal the surface speed of the engraved roll. Furthermore, the rotation of the rolls must be in the same direction as the movement of the matrix.

Other methods of impregnating the matrix with measured amounts of treatment solution, such as by spraying, dipping, extrusion or by reverse roll, may also be used.

The coating/impregnation method described above enables a uniform and accurate application of all active ingredients to the woven or nonwoven matrix of natural and/or synthetic fibers foam without the use of carriers and without the need for a separate step to dry the residual diluted solutions from the matrix.

Evaluation and testing of the wipe and other products of the present invention, as detailed in the examples included hereinafter, clearly establishes that the invention products differ from products found in the prior art in a number of ways. The formulation described and claimed herein consists of active ingredients only and no fillers, buffers or diluents are used. The particular active ingredients noted are dissolved in a non-aqueous component, thereby obviating the need for buffers, stabilizers and preservatives which are generally used in aqueous solutions.

An additional feature and benefit of the present invention resides in the use of a single treated matrix which is capable of being used in a variety of applications. Using the present invention, one can clean and/or disinfect skin, remove dust from an air stream, or decontaminate spills.

The following examples are illustrative of the present invention. Unless the context indicates otherwise, all percentages herein are by weight and based on the weight of the matrix.

EXAMPLE I

Into a 5-liter kettle were added 1740 grams of propylene glycol and 60.0 grams of IGEPAL CO–660, a non ionic ethoxyalated nonylphenol surfactant from Rhone-Poulenc or an equivalent surfactant such as Surfactol NP-10 from Surfactants, Inc. The mixture was stirred for a few minutes until the surfactant was completely dissolved and a homogeneous solution resulted. To this stirred solution was added slowly over 15 minutes, 200 grams of povidone-iodine from BASF Corporation. The solution was stirred for two hours or until no particles of povidone-iodine were visible and no additional increase in viscosity was observed. After standing for 24 hours an aliquot from the dark reddish homogeneous solution displayed a specific gravity of 1.060. It was analyzed for active iodine by titration and found to exhibit a 1.13% active iodine concentration. One gram of this solution in 9 grams of water (10% concentration) displayed a pH of 2.6.

10% Solution of Povidone-Iodine in Propylene Glycol

| Ingredients | Weight percent |
| --- | --- |
| PVP-Iodine | 10.0% |
| Propylene glycol | 87.0% |
| IGEPAL CO-660 | 3.0% |

A non-woven commercial web of thermally bonded 50% rayon: 50% polypropylene fibers with a basis weight of 14 grams per square yard was wound on a three inch core.

The matrix is placed on an unwind stand and directed through an impregnating station consisting of an engraved printing roll having a pattern capable of applying the desired amount of treating solution to the matrix. The engraved roll is partially immersed in the treating solution described above such that as the roll turns it picks up treating solution from the pan containing same and transfers this solution to the nonwoven matrix. To assure proper transfer to the nonwoven matrix, a pressure roll may be mounted above the engraved roll. The process described above is commonly called a "printing" process.

The nonwoven matrix is run through the printing process and picks up 50% of the treating solution, based on the basis weight of the matrix.

Another web of 70% rayon: 30% polyester with a basis weight of 31 grams per square yard was treated in the same manner with the above povidone iodine solution.

Each of the rolls of treated nonwoven matrix was run through a Hudson-Sharp automatic folding machine which yielded wipes which were quarter folded. When each of these treated fabrics were rubbed on skin, the treatment readily transferred from substrate to skin as evidenced by the lubricious feel and shine imparted to the skin by the propylene glycol. No discoloration of skin from povidone-iodine was observed.

Bactericidal efficacy studies of these prototype dairy wipes were conducted in vitro by rubbing the treated wipes on slides previously inoculated with $10^6$ colony forming units per milliliter (cfu/ml) of streptococcus agalactiae, staphylococcus aureus and streptococcus uberis, respectively. The percent reduction in cfu versus time are shown in Table I.

TABLE I

Percent Reduction in CFU Using Wipes Treated with 10% PVP-Iodine Formulation.

| Fabric | streptococcus agalactiae | | staphylococcus aureus | | streptococcus uberis | |
| --- | --- | --- | --- | --- | --- | --- |
| | 1 min. | 5 min. | 1 min. | 5 min. | 1 min. | 5 min. |
| 0.5 oz/yd 50% rayon:50% PP | 99 | 99.1 | 96.9 | 98.2 | 94.6 | 97.0 |
| 1.1 oz/yd 70% rayon:30% polyester | 99.1 | 99.4 | 97.1 | 98.9 | 95.0 | 98.1 |

Table I shows that the dairy wipes treated with the 10% PVP-iodine solution in propylene glycol exhibit effective in vitro germicidal activity.

Treatment of a nonwoven rayon-polyester substrate with a 10% solution of PVP-iodine in propylene glycol at add on levels below 40% did not produce a wipe sufficiently impregnated to transfer the active solution from the substrate to skin. When the add on levels were increased to >50%, the treatment transferred readily from wipe to skin and showed high germicidal activity in vitro. This technology of a propylene glycol pre-activated germicidal wipe capable of transferring treatment without the need for water activation distinguishes this invention from previous products. The present invention provides the technology necessary to apply a germicidal agent via a wipe to cow's teats to control mastitis, without the intervention of water.

EXAMPLE II

Propylene glycol, 92.0 grams, was combined with 3.0 grams of Surfactol NP-10, a non-ionic ethoxylated nonylphenol surfactant from Surfactants, Inc., in a 500 ml jar. The ingredients were mixed together until a homogeneous solution was produced. Five grams of PVP-iodine from BASF Corporation were slowly added over 15 minutes to the propylene glycol solution and the contents were well stirred until a homogeneous solution of the PVP-iodine as evidenced by no visible particles of PVP-iodine and no further increase in the viscosity of the solution.

The dark reddish solution was characterized by its specific gravity measured as 1.049, its pH of a 10% solution in water of 3.2 and its active iodine concentration of 0.57% by titration.

5% Formulation of PVP-Iodine in Propylene Glycol

| Ingredients | Weight Percent |
| --- | --- |
| PVP-iodine | 5.0% |
| Propylene glycol | 92.0% |
| Surfactol NP-10 | 3.0% |

This 5% PVP-iodine solution in propylene glycol was placed in a hand held Preval Power sprayer unit and sprayed onto the surface of several pieces of 10"×10" fabric of a non-woven material of 70% rayon, 30% polyester with a basis weight of 1.1 oz/yd². The non-woven fabric was treated with the PVP-iodine solution until it had picked up 50% of its weight in treatment. Another non-woven fabric with a basis weight of 0.5 oz/yd² constructed from 50% rayon, 50% polypropylene was treated with the PVP-iodine solution in a similar manner.

Both fabrics when rubbed on skin transferred the treatment readily as evidenced by the lubricious feel and shine on the skin imparted by the propylene glycol. No discoloration of the skin from the PVP-iodine was observed.

The germicidal efficacy of these treated wipes were measured in vitro against $10^6$ cfu/ml of streptococcus agalactiae, staphylococcus aureus and streptococcus uberis inoculated onto glass slides respectively. The slides were rubbed with the treated wipes and the remaining cfu were measured versus time. Table II shows the results of this germicidal efficacy test.

TABLE II

Percent Reduction in CFU Using Wipes Treated with 5% PVP-Iodine Formulation.

| Fabric | streptococcus agalactiae | | staphylococcus aureus | | streptococcus uberis | |
|---|---|---|---|---|---|---|
| | 1 min. | 5 min. | 1 min. | 5 min. | 1 min. | 5 min. |
| 0.5 oz/yd 50% rayon:50% PP | 98.2 | 99.2 | 96.1 | 98.5 | 90.2 | 96.7 |
| 1.1 oz/yd 70% rayon:30% polyester | 98.3 | 99.0 | 95.4 | 99.3 | 93.4 | 96.5 |

Table II shows that the wipes treated with 5% PVP-iodine formulation exhibited substantial germicidal activity.

Formulations of PVP-iodine in propylene glycol can be prepared from as low a concentration of 1% PVP-iodine (0.1% active iodine) to a high of 15% PVP-iodine (1.5% active iodine). Higher concentrations are difficult to prepare due to the limits of solubility of PVP-iodine in propylene glycol and the high viscosity of these solutions.

EXAMPLE III

A matrix, comprising three sonically-bonded layers of a commercially available nonwoven web of polypropylene fibers wherein the polypropylene fibers in each layer are thermally bound together and possess a basis weight of 10 to 15 grams per square yard and was prepared so that the resultant bonded matrix had a basis weight of between 30 and 45 grams per square yard, was wound on a three inch core.

The matrix is placed on an unwind stand and directed through an impregnating station consisting of an engraved printing roll having a pattern capable of applying the desired amount of treating solution to the matrix. The engraved roll is partially immersed in the treating solution such that, as the roll turned, it picks up treating solution from the pan containing same and transferred the solution to the nonwoven matrix. To assure proper transfer to the nonwoven matrix, a pressure roll may be mounted above the engraved roll. The process described above is commonly called a "printing" process.

The nonwoven matrix is run through the printing process and picking up at least about 50% of the treating solution, based on the basis weight of the matrix.

For the purpose of this example, after treatment, the roll of treated nonwoven matrix was run through a Hudson-Sharp automatic folding machine which yielded wipes which were quarter folded. The resultant wipes were capable of being used as dust cloths.

EXAMPLE IV

Propylene glycol, 96.5 grams, was combined with 3.0 grams of a non-ionic surfactant, Surfactol NP-10 an ethoxylated nonyl phenol in a jar. The liquids were stirred until a clear homogeneous solution was produced. Into this solution was added 0.5 grams of chlorhexidine diacetate from Degussa. The chlorhexidine diacetate dissolved quickly and a clear, colorless solution resulted. The pH of a 10% solution in water was 6.7 and the specific gravity of the 0.5% chlorhexidine solution in propylene glycol was 1.040.

The 0.5% chlorhexidine diacetate solution in propylene glycol was sprayed onto the surface of several pieces of a 10"×10", 1.1 oz/yd² non-woven fabric of 70% rayon, 30% polyester and also several pieces of a non-woven fabric of 0.5 oz/yd² composed of 50% rayon, 50% polypropylene. Each of the pieces of fabric were sprayed until they picked up 50% by weight of the treatment. The treated fabrics were stored in black plastic bags to minimize photo degradation of the chlorhexidine diacetate.

0.5% Solution of Chlorhexidine Diacetate in Propylene Glycol

| Ingredients | Weight percent |
|---|---|
| Chlorhexidine diacetate | 0.50% |
| Propylene glycol | 96.5% |
| Surfactol NP-10 | 3.0% |

Both fabrics transferred the treatment readily when rubbed on skin as evidenced by the glistening and shine imparted by the propylene glycol. The germicidal efficacy of these treated wipes were measured in vitro against $10^6$ cfu/ml of streptococcus agalactiae, staphylococcus aureus and streptococcus uberis inoculated onto glass slides respectively. The slides were rubbed with the treated wipes and the remaining cfu were measured versus time. Table III shows the results of this germicidal efficacy test.

TABLE III

Percent Reduction in CFU Using Wipes Treated with 0.5% Chlorhexidine Diacetate Formulation

| Fabric | streptococcus agalactiae | | staphylococcus aureus | | streptococcus uberis | |
|---|---|---|---|---|---|---|
| | 1 min. | 5 min. | 1 min. | 5 min. | 1 min. | 5 min. |
| 0.5 oz/yd 50% rayon:50% PP | 93.4 | 97.6 | 94.8 | 97.4 | 90.2 | 95.3 |
| 1.1 oz/yd 70% rayon:30% polyester | 95.6 | 98 | 96.8 | 98.0 | 93.4 | 95.5 |

Table III shows that the wipes treated with 0.50% chlorhexidine exhibited germicidal activity.

EXAMPLE V

For in vitro germicidal dairy wipe activity studies as well as dairy wipe in vivo post milking herd studies to prevent mastitis, two concentrations of PVP-iodine in propylene glycol were prepared from which roll goods were treated.

An in vivo post milking herd study with PVP-iodine and chlorhexidine diacetate treated wipes to measure their efficacy in controlling mastitis was conducted. The study was divided into 5 cells with 30 cows in each cell. Cell 1 is a negative control, the cows in this group received no post milking treatment. Cell 2 is a positive control in which each cow was treated with a leading commercial post milking teat dip. In cell 3, the cow's teats were wiped post milking with a germicidal dairy wipe treated with 0.5% chlorhexidine diacetate. In cell 4, the teats were wiped post milking with a 5% PVP-iodine germicidal wipe and in cell 5 the cows' teats were treated with a 10% PVP-iodine dairy wipe. Table IV below shows the number of cows with new intra-mammary infections in each of the cells after an 8 week study was completed.

TABLE IV

NEW INTRA-MAMMARY INFECTIONS

|  | Cell 1 | Cell 2 | Cell 3 | Cell 4 | Cell 5 |
|---|---|---|---|---|---|
| Eligible Quarters | 120 | 120 | 120 | 120 | 120 |
| New Infections After 8 Weeks | 60 | 19 | 24 | 19 | 18 |

Table IV shows that the PVP-iodine wipes performed at parity with the leading commercial teat dip and that the chlorhexidine wipes performed slightly below parity with the leading commercial dip.

What we claim is:

1. A substantially anhydrous antimicrobial solution consisting essentially of at least one antimicrobial selected from the group consisting of PVP-iodine and chlorhexidine diacetate in solution in a glycol, wherein said solution can be safely applied to skin.

2. The antimicrobial solution of claim 1 wherein said solution has between about 1 and 15% PVP-iodine.

3. The antimicrobial solution of claim 1 further including between about 1 and 15% of a nonionic surfactant.

4. A wipe comprising a flexible substantially dry matrix, said matrix comprising natural or synthetic, woven, non-woven or knitted fibers, said matrix having been coated or impregnated with a substantially anhydrous antimicrobial treatment solution in an amount sufficient to allow said matrix to retain its substantially dry characteristics, consisting essentially of an effective amount of at least one antimicrobial selected from the group consisting of PVP-iodine and chlorhexidine diacetate in solution in a glycol, wherein said wipe feels lubricious to the skin.

5. The wipe of claim 4 in which said matrix is in a form selected from the group consisting of a woven fabric, a non-woven fabric and a knitted fabric.

6. The wipe of claim 4 in which at least about 60% of the solvent of said treatment solution is propylene glycol.

7. The wipe of claim 5 in which said matrix contains between about 50 and 70 percent rayon and between about 30 and 50 percent polyester.

8. The wipe of claim 4 in which the weight of said treatment solution in said matrix is at least about 40%, but less than about 60% of the weight of said matrix.

9. The wipe of claim 4 in which the fabric basis of said matrix is between about 14 and 85 gm/yd$^2$.

10. The wipe of claim 4 in which said wipe further contains between about 0 and 15% of a non-ionic surfactant.

11. The wipe of claim 4 in which said antimicrobial is PVP-iodine and the level of PVP-iodine is between about 1 and 15% of said treatment solution.

12. The wipe of claim 11 in which the level of PVP-iodine is between about 5 and 10% of said treatment solution.

13. A method of milking a cow to prevent transfer of microbes among the herd comprising the steps of
 a) wiping each of the cow's teats with a wipe according to claim 4 whereby said antimicrobial solution is transferred to said teats, and
 b) attaching the milking machine to the cow's teats.

14. The method of claim 13 further comprising the step of rewiping the cow's teats after milking.

15. The method of claim 13 further comprising the step of cleaning each of said cow's teats with said wipe.

16. The wipe of claim 13 in which the weight of said non-aqueous treatment solution in said matrix is at least about 40%, but less than about 60% of the weight of said matrix.

17. The method of claim 13 in which said antimicrobial component is PVP-iodine and at least about 5 percent of the treatment solution is PVP-iodine.

18. The method of claim 17 in which said PVP-iodine is less than about 15 percent of the non-aqueous solution.

19. The method of claim 13 in which said wipe is disposed of after use on a single cow.

20. The antimicrobial solution of claim 1 impregnated into a fabric in a manner effective to impart antimicrobial activity to said fabric, said fabric being a part of a member selected from the group consisting of surgical gowns, surgical drapes, surgical towels, bandages and sponges.

21. The wipe of claim 5 in which said matrix contains synthetic or natural fibers, or blends thereof.

* * * * *